United States Patent
Hillendahl et al.

(10) Patent No.: US 8,985,808 B2
(45) Date of Patent: Mar. 24, 2015

(54) UNIFORM EPI-ILLUMINATION OF PLANAR SAMPLES

(71) Applicant: Bio-Rad Laboratories, Inc., Hercules, CA (US)

(72) Inventors: James W. Hillendahl, Vacaville, CA (US); Evelio Perez, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 224 days.

(21) Appl. No.: 13/740,590

(22) Filed: Jan. 14, 2013

(65) Prior Publication Data
US 2013/0223056 A1  Aug. 29, 2013

Related U.S. Application Data

(60) Provisional application No. 61/604,946, filed on Feb. 29, 2012.

(51) Int. Cl.
| | |
|---|---|
| *F21S 4/00* | (2006.01) |
| *F21V 21/005* | (2006.01) |
| *F21V 9/08* | (2006.01) |
| *F21V 13/02* | (2006.01) |
| *G01N 21/64* | (2006.01) |

(52) U.S. Cl.
CPC ............ *F21V 21/005* (2013.01); *F21V 9/083* (2013.01); *F21V 13/02* (2013.01); *G01N 21/6452* (2013.01); *G01N 2021/6463* (2013.01); *G01N 2201/06* (2013.01); *G01N 2201/0626* (2013.01); *G01N 2201/0635* (2013.01)
USPC .......................................................... 362/223

(58) Field of Classification Search
CPC ....................................................... F21V 13/02
USPC .......................................................... 362/223
See application file for complete search history.

(56) References Cited

U.S. PATENT DOCUMENTS

| | | | |
|---|---|---|---|
| 4,447,126 A | 5/1984 | Heidrich et al. | |
| 7,491,924 B2 | 2/2009 | Oldham et al. | |
| 2004/0203164 A1* | 10/2004 | Cizdziel et al. | 436/95 |
| 2007/0031150 A1 | 2/2007 | Fisher et al. | |
| 2007/0035734 A1 | 2/2007 | Müller et al. | |
| 2010/0075409 A1 | 3/2010 | Waiche | |

(Continued)

OTHER PUBLICATIONS

International Search Report and Written Opinion from PCT/US2013/021378 dated Mar. 25, 2013.

*Primary Examiner* — Anh Mai
*Assistant Examiner* — Hana Featherly
(74) *Attorney, Agent, or Firm* — Kilpatrick Townsend & Stockton LLP

(57) ABSTRACT

A planar sample, particularly of the type used in biological laboratories for detection and sometimes analysis of two-dimensional arrays of proteins, nucleic acids, or other biological species, is illuminated by epi-illumination using optically filtered line lights that are arranged along opposing parallel sides of a rectangle in which the sample array resides, with two coaxial line lights on each side of the rectangle, and the two on any given side being separated by a gap whose optimal width depends on the wavelength band transmitted by the optical filter. Surprisingly, the gap eliminates the peak in intensity at the center of the sample area and the decrease that occurs from the center outward that would otherwise occur with a single continuous filtered line light, producing instead a substantially uniform intensity along the direction parallel to the line lights.

31 Claims, 3 Drawing Sheets

(56) References Cited

U.S. PATENT DOCUMENTS

| | | |
|---|---|---|
| 2010/0142041 A1 | 6/2010 | Berman |
| 2010/0261197 A1 | 10/2010 | Goldberg et al. |
| 2011/0116261 A1 | 5/2011 | Brukilacchio et al. |
| 2011/0236985 A1 | 9/2011 | Boday et al. |

* cited by examiner

UNIFORM EPI-ILLUMINATION OF PLANAR SAMPLES

CROSS-REFERENCE TO RELATED PATENT APPLICATIONS

The present application claims benefit of priority to U.S. Provisional Patent Application No. 61/604,946, filed on Feb. 29, 2012, which is incorporated by reference.

BACKGROUND OF THE INVENTION

Studies of DNA and proteins in biological laboratories often involve the fluorescence imaging of planar samples of moderate to large area, such as those ranging from 5 cm×5 cm up to 26 cm×26 cm. Common examples of these samples are electrophoresis gels and blotting membranes. The imaging is often performed by camera-based instruments that include an excitation light source of different wavelengths, depending on the sample matrix and the species sought to be detected within the matrix. Gels for example are substantially transparent to ultraviolet (UV), visible, and near infrared (NIR) light, and can be detected from above with illumination from below in the "trans" mode, i.e., by a transilluminator. Transillumination is typically performed with UV-B light in conjunction with a filter that blocks visible-range wavelengths and transmits UV wavelengths, or with phosphor light conversion plates, plastic light conversion plates, or both, to convert the UV light into visible light. Examples of these plates are the XCITABLUE™ Conversion Screen of Bio-Rad Laboratories, Inc. (Hercules, Calif., USA), and the UV/White Light Conversion Screen of UVP, LLC (Upland, Calif., USA). Gels can also be illuminated from above, i.e., on the same side where detection is performed, in the "epi" mode. Epi-illumination is typically performed with an optically filtered light source, which can be either a bulb or an LED. Blot samples for example are optically opaque in the UV, visible, and NIR ranges and must be epi-illuminated.

Epi-illumination imaging systems are sold by Bio-Rad Laboratories, Inc., Fuji Manufacturing USA, Inc. (Greenwood, S.C., USA), GE Healthcare Bio-Sciences, Inc. (Piscataway, N.J., USA), Syngene (Frederick, Md., USA), and ProteinSimple (Santa Clara, Calif., USA). While both light-emitting diodes (LEDs) and bulbs can be used, LEDs are highly favored since they offer high spectral purity and intensity. The illumination produced by LED illuminators is highly non-uniform illumination, however, with a typical radial reduction in intensity of 90% or more from the center of the sample to the edge. This presents a challenge, because non-uniform sample illumination results in a correspondingly non-uniform sample signal which must be made uniform by flat fielding using calibration samples and software. Flat fielding is also used to remove the effects of lens roll-off and optical filter roll-off, both with angle. A single technique such as flat fielding is not well equipped to address all three effects—illumination non-uniformity, lens roll-off, and optical filter roll-off. What is needed therefore is a means of achieving highly uniform illumination, leaving lens and filter roll-off issues to flat fielding which more effectively addresses these issues.

SUMMARY OF THE INVENTION

The present invention stems, at least in part, from the discovery that LED line lights, when used in conjunction with optical bandpass filters, as such lights commonly are, and when placed end-to-end to extend the length of the illuminated area, do not produce a uniform light intensity along their combined lengths. Instead, the intensity produced in the region of the junction between the two line lights is significantly higher than that produced in neighboring regions. It has accordingly been discovered that this nonuniformity can be substantially reduced or eliminated by placing a gap between the two line lights, with no light source within the gap. The result is two adjacent and coaxial line lights separated by a gap, that when placed above a planar sample at a sufficient distance to illuminate the entire sample produce illumination that is substantially uniform along their combined lengths despite the gap. Uniformity of intensity in the transverse direction, i.e., the direction perpendicular to the line of the line lights, is achieved by placing the pair above and to one side of the sample and another pair of line lights above and to the other side of the sample, at the same height and distance. While each side individually produces an intensity that decreases as one travels from the side of the sample area closest to the light source to the other side, the combined illuminations from both sides complement each other by superimposing gradients of opposite directions to achieve a total that is at least substantially uniform.

Further features, aspects, objects, and embodiments of the invention will be apparent from the descriptions that follow.

DETAILED DESCRIPTION OF SELECTED EMBODIMENTS

Figure 1:
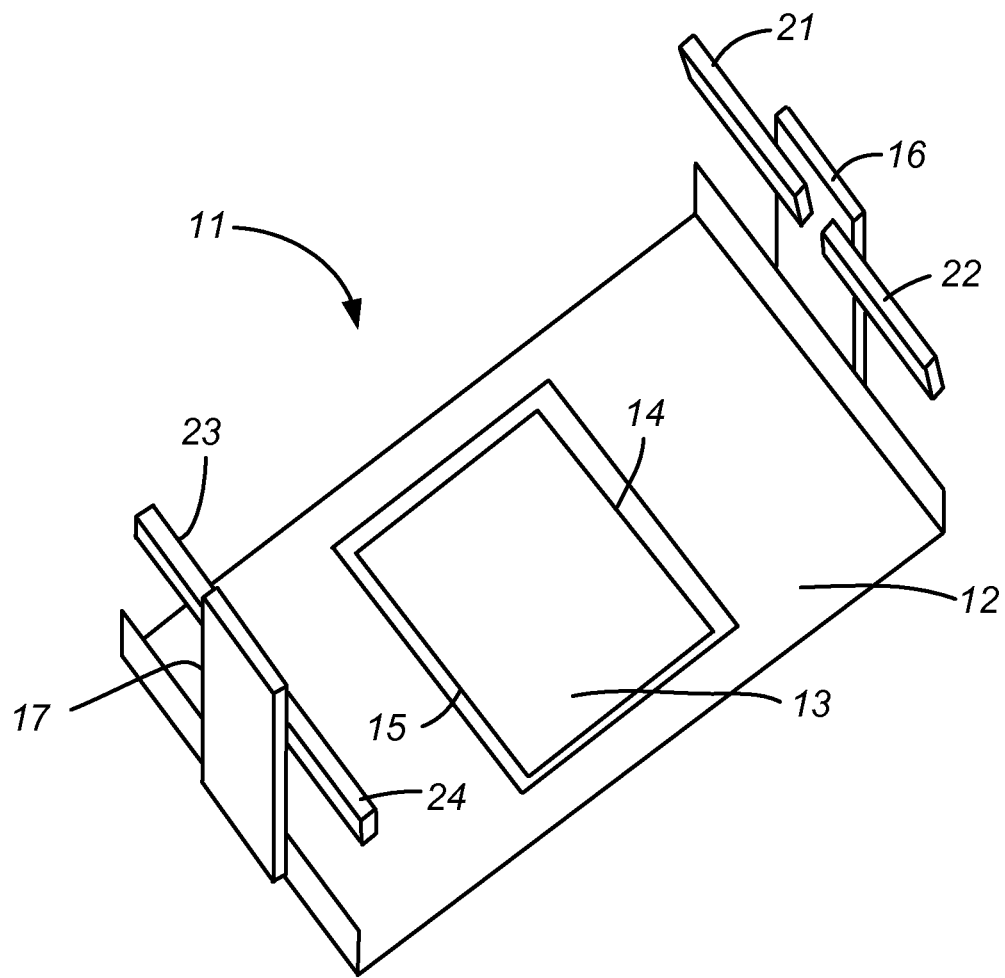
FIG. 1 is a perspective view of one example of an epi-illuminator in accordance with the present invention.

High-intensity LED line lights are commercially available from a variety of suppliers. Examples are Edmund Optics Inc. of Barrington, N.J., USA, ProPhotonix Limited of Salem, N.H., USA, and Advanced Illumination, Inc., of Rochester, Vt., USA. The typical LED line light is a linear array of individual LEDs evenly spaced with approximately 0.5 mm between each adjacent pair in the array. In certain embodiments of the invention, however, the non-uniform spacings between individual LEDs can be beneficial, for example when significant decreases in intensity (intensity "roll-offs") occur at the outer ends of the paired line lights. A spacing that decreases in the direction of the outer end can compensate for these decreases to assure that uniformity of intensity continues along the entire combined lengths of the two line lights, in addition to the region of the gap between the two line lights. The variation in spacing is readily determined by routine experimentation.

The length of each individual line light can vary and is not critical to the present invention, nor does it affect the optimal width of the gap between the coaxial line lights. Factors affecting the choice of length will typically be the dimensions of the sample to be illuminated and the lengths of commercially available line lights. For most electrophoresis gels and blotting membranes, line lights that are from about 50 mm to about 500 mm in length will suffice, or alternatively from about 75 mm to about 150 mm. An example is a line light that is 100 mm in length.

While a single pair of line lights on each side of the sample will suffice in most cases due to the lengths of available line lights and the typical dimensions of a planar sample, the present invention is not limited to a single pair per side, but instead applies to two or more per side, with the aforementioned gap between each adjacent pair.

The gap between the adjacent and coaxial line lights will be of a width that will cause the line lights on either side of the gap to produce illumination of the sample area that is substantially uniform in intensity along the direction parallel to the line lights. The width can vary with the distance between the line light and the sample, and the width can also vary with the location of the optical filter transmission band in the spectrum. With wavelength bands centered on shorter wavelengths, a smaller gap will provide the best results, and with bands whose absorption curves are relative narrow, a smaller gap may be needed for these as well. Thus, a green filter will require a smaller gap than a red filter, and a blue filter will require a smaller gap than both a red filter and a green filter. For a red filter producing a band centering on 625 nm, for example best results in most cases will be achieved with a width that is from about 70 mm to about 110 mm, and in many cases from about 80 mm to about 85 mm.

In certain cases, light-blocking baffles can be included to further improve the uniformity of the light intensity, particularly in the region of the gap, by shielding a portion of the light from the line lights from entering the central region of the sample area. Baffles can be placed for example at the inner ends of the line lights, i.e., immediately adjacent to the gap, and protruding toward the centerline of the sample area. For a gap of whose width is within the range of about 70 mm to about 110 mm, each baffle may extend forward by a distance within the range of about 2 cm to about 5 cm. The need for baffles will be greater for gaps that are closer together.

For epi-illumination, the line lights will be above and to the sides of the sample area to leave access to the sample area for imaging components that are also positioned above the sample area. The light from the line lights will thus strike the sample area at acute angles, thereby creating the need as stated above for line lights symmetrically arranged on both sides of the sample area, i.e., a coaxial pair of line lights on each side with gaps between the two members of the each coaxial pair. All line lights on both sides will be parallel, and for a sample area that is rectangular in shape with two opposing parallel sides, all line lights will be parallel to the parallel sides of the sample area. The distance between each line light and the sample area can be expressed in terms of the centerline of the sample area, i.e., the straight line within the sample area that is parallel to and midway between both parallel sides of the sample area. While the distance between each line light and this centerline can vary, it will generally be the same for all line lights, and in most cases best results will be obtained when this distance is from about 10 cm to about 25 cm. To obtain uniform intensity in the direction transverse to the axes of the line lights, the line lights will be symmetrically arranged relative to the sample area. Once the line lights are positioned to achieve the complementary effect of their intensities (and hence a uniform total intensity) along the transverse direction, the distance between each line light and the centerline as well as the angle of each line light relative to the plane of the sample area can vary while still maintaining the uniformity. This can be achieved by maintaining the symmetrical placement and by limiting the variation to positions along a hyperbolic line. Thus, a plane intersecting the line lights and sample area in a direction perpendicular to the axes of the lights will intersection those axes and the sample area centerline at three points, and a hyperbola defined by those three points delineates the locations along which the line lights can be placed.

Any of a variety of optical bandpass filters can be used, depending on the fluorophores in the sample, the type and requirements of the assay that is performed on the sample prior to optical detection, and the choice of the user. Examples of transmission wavelength ranges for the filter are about 460 nm to about 480 nm, about 520 nm to about 540 nm, about 615 nm to about 635 nm, about 670 nm to about 690 nm, and about 760 nm to about 780 nm. Elongated optical filters at these wavelength ranges that are suitable for line lights are commercially available, as are multi-color filters mounted, for example on rotatable turrets, allowing the user to make selections for individual applications. Filters of different colors can also be mounted at different heights on the parabola mentioned in the preceding paragraph. Further refinement of the light transmitted by the filters, including enhancement of the uniformity in intensity, can be achieved by adding graduated neutral density filters between the optical density filters and the sample area.

Unfiltered line lights will produce light output spanning a full 180-degree angle, but optical bandpass filters will often reduce this angle to 40 degrees, equal to 20 degrees optical (i.e., 20 degrees on each side of the axis of the beam). In many cases, the functional angle of the light emerging from the filter will be 30 degrees, or 15 degrees optical. The inventors herein have discovered that this decrease in functional angle when used with line lights of at least 50 mm in length results in a significantly greater intensity at the center of the line light relative to the ends, and a gradient in intensity between the center and the ends, the difference and gradient being considerably more greater than any observed with unfiltered line lights.

The line lights will be positioned so that they form a wedge angle with the rectangular sample area, and for optimal results, the wedge angle will be equal to or less than the functional angle of light emerging from the filter. The emerging light will therefore illuminate the entire sample area within the functional angle. The wedge angle itself can vary with the choice of filter and the dimensions of the sample area. In most cases, best results will be obtained with a wedge angle within the range of from about 15 degrees to about 30 degrees.

A further variation can be achieved by placing a negative lens between each line light and the sample area, or between each optical filter and the sample area. Bi-concave or plano-concave lenses can adjust or optimize the light intensity profile. Still further variations will be readily apparent to those of skill in the art.

Figure 2:
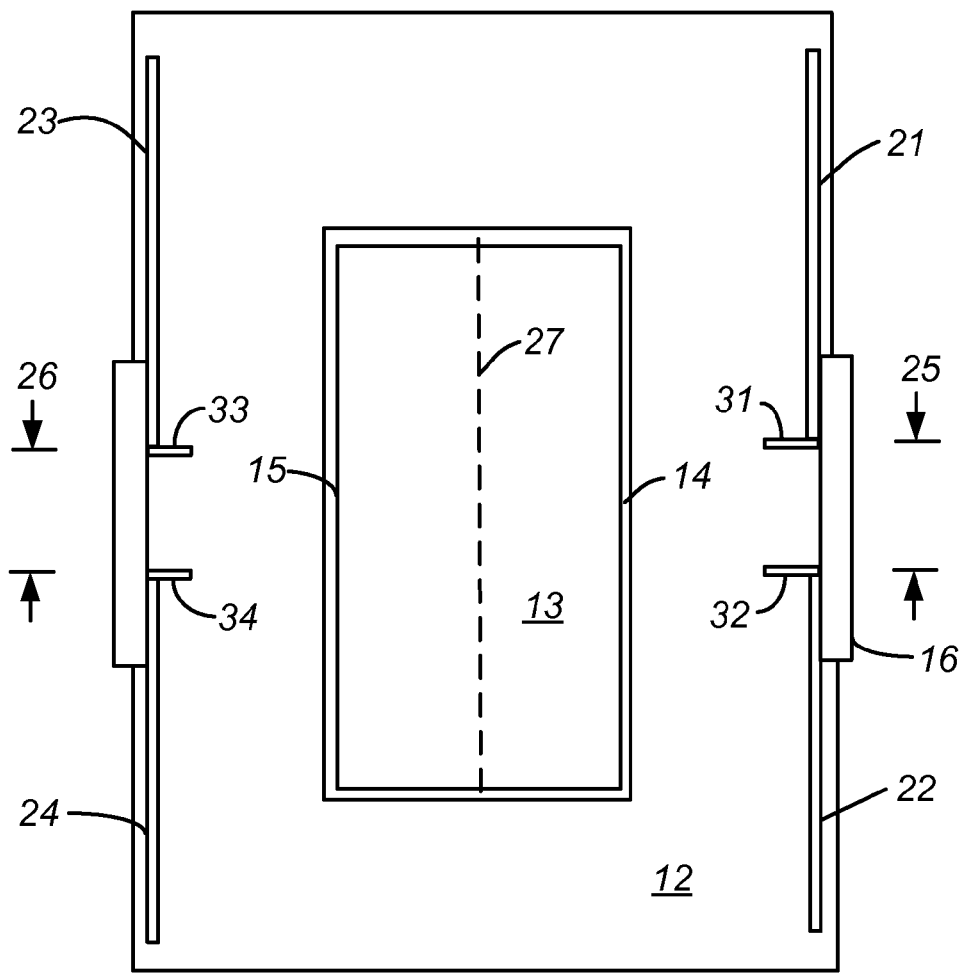
FIG. 2 is a top view of the epi-illuminator of FIG. 1.

FIG. 1 is an perspective view from above of an epi-illuminator 11 representing one illustrative embodiment of the present invention. The illuminator has a planar platform 12 with a designated sample area 13 within the area of the planar platform, the sample area having two opposing parallel sides 14, 15. Raised above and to the sides of the sample area at two racks or supports 16, 17 to which are mounted line lights 21, 22, 23, 24. A plan view of the illuminator is presented in FIG. 2. The line lights 21, 22, 23, 24 are each arranged parallel to the opposing sides 14, 15 of the sample area, with a pair of line lights on each side, the two in each pair being coaxial and separated by the gap 25, 26 as described above. The centerline 27 of the sample area is indicated by a dashed line. The baffles 31, 32, 33, 34 are shown at the inner ends of the line lights.

Figure 3:
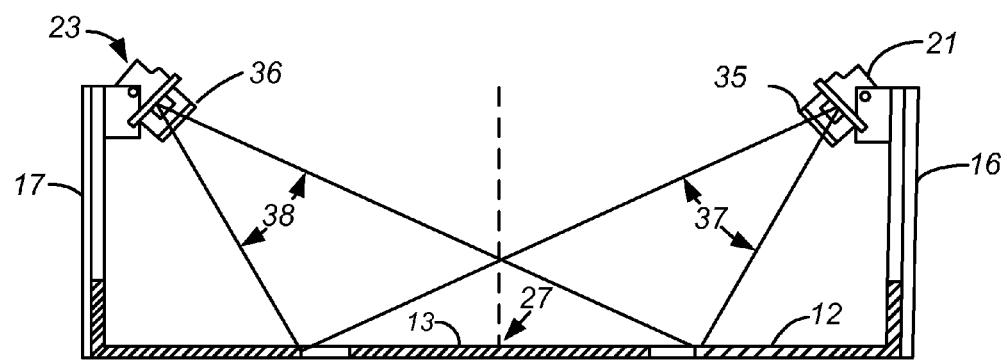
FIG. 3 is a vertical cross section of the epi-illuminator of FIG. 1.
Figure 4:
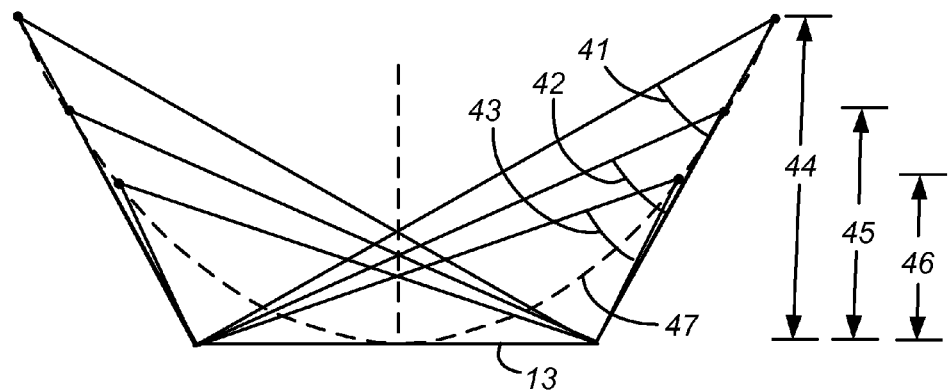
FIG. 4 is a diagram of multiple locations for the line lights of the epi-illuminator of FIG. 1.

FIG. 3 is a vertical cross section of the illuminator, showing two of the four line lights 21, 23, the optical bandpass filters 35, 36 associated with each of the line lights, and the wedge angles 37, 38 of light being transmitted from the optical filters. As the Figure illustrates, the light striking the sample area from each individual line light decreases in intensity from the near side of the sample area to the far side due to the greater distance that the light must travel, and since the decrease in light intensity from the line light on the opposing side is in the opposite direction, the two intensity gradients cancel each other out to provide a uniform intensity along the entire width of the sample area along the left-to-right dimension. FIG. 4 shows a number of different various wedge angles 41, 42, 43 obtained by placing the line lights at different heights 44, 45, 46. The apex of each wedge represents the light emerging from the optical filters. As noted above, if the filtered line lights are pointed in directions such that the wedge angles will encompass the entire width of the sample area, the complementarity that will result in a uniform intensity along the width of the sample area will be achieved in the positions of the filtered line lights remain along a parabolic curve 47.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An epi-illuminator for a planar sample, said epi-illuminator comprising:
    a planar platform with a designated sample area thereon that contains said planar sample;
    LED line lights mounted above said planar platform when said planar platform is horizontal, with at least two said line lights positioned along, and parallel to, each of two opposing parallel sides of said sample area and an optical bandpass filter between each said line light and said sample area, each said line light arranged to produce, through said optical bandpass filter, a wedge-shaped light beam intersecting said sample area at acute angles and spanning said sample area in a direction transverse to said line lights, with line lights on opposing sides of said sample area complementing each other to produce a combined illumination of said sample area that is substantially uniform in intensity along said transverse direction; and
    a gap separating said two line lights along each of said parallel sides of said sample area, said gap being of a width sufficient to produce a combined illumination of said sample area from said line lights that is substantially uniform in intensity along a direction parallel to said line lights.

2. The epi-illuminator of claim 1 wherein said gap is from about 70 mm to about 110 mm.

3. The epi-illuminator of claim 1 wherein said gap is from about 80 mm to about 85 mm.

4. The epi-illuminator of claim 1 wherein each of said line lights is from about 75 mm to about 150 mm in length.

5. The epi-illuminator of claim 1 wherein said sample area has a centerline that is parallel to and midway between each of said parallel sides, and each of said line lights is at a distance of from about 10 cm to about 25 cm from said sample area centerline.

6. The epi-illuminator of claim 5, wherein the line lights are arranged symmetrically relative to the centerline.

7. The epi-illuminator of claim 5, wherein the distance between each line light and the centerline is the same for all line lights.

8. The epi-illuminator of claim 1 wherein each said wedge-shaped light beam intersects said parallel sides to form a wedge angle of from about 15 degrees to about 30 degrees.

9. The epi-illuminator of claim 1 wherein said optical bandpass filter passes light within a wavelength range of about 460 nm to about 480 nm.

10. The epi-illuminator of claim 1 wherein said optical bandpass filter passes light within a wavelength range of about 520 nm to about 540 nm.

11. The epi-illuminator of claim 1 wherein said optical bandpass filter passes light within a wavelength range of about 615 nm to about 635 nm.

12. The epi-illuminator of claim 1 wherein said optical bandpass filter passes light within a wavelength range of about 670 nm to about 690 nm.

13. The epi-illuminator of claim 1 wherein said optical bandpass filter passes light within a wavelength range of about 760 nm to about 780 nm.

14. The epi-illuminator of claim 1 wherein each of said line lights comprises LEDs evenly spaced apart.

15. The epi-illuminator of claim 1 wherein each of said line lights comprises LEDs with nonuniform spacing to avoid decreases in light intensity at outer ends of uniformly spaced line lights.

16. The epi-illuminator of claim 1 wherein each of said optical bandpass filters comprises a plurality of filters of different wavelength bands mounted on a rotatable turret.

17. The epi-illuminator of claim 1 wherein graduated neutral density filters are positioned between said optical bandpass filters and said sample area.

18. The epi-illuminator of claim 1 further comprising light-blocking baffles affixed to inner ends of each of said line lights adjacent to said gaps and extending toward said sample area.

19. The epi-illuminator of claim 1 further comprising a negative lens between each line light and said sample area.

20. The epi-illuminator of claim 1, wherein the at least two line lights positioned along each side of the sample area are coaxial.

21. A method for illuminating a planar sample, said method comprising:
    (a) placing said sample on a planar platform within a sample area of said platform; and
    (b) illuminating said sample with LED line lights positioned above said sample area, with at least two said line lights positioned along, and parallel to, each of two parallel sides of said sample area, while filtering said line lights with an optical bandpass filter, each said line light positioned to produce, through said optical bandpass filter, a wedge-shaped light beam intersecting said sample area at acute angles and spanning said sample area in a direction transverse to said line lights, and with line lights on opposing sides of said sample area complementing each other to produce a combined illumination of said sample area that is substantially uniform in intensity along said transverse direction, and with said two line lights along each of said parallel sides of said sample area separated by a gap of a width sufficient to produce a combined illumination of said sample area from said line lights that is substantially uniform in intensity along a direction parallel to said line lights.

22. The method of claim 21 wherein said gap is from about 70 mm to about 110 mm.

23. The method of claim 21 wherein said gap is from about 80 mm to about 85 mm.

24. The method of claim 21 wherein each of said line lights is from about 75 mm to about 150 mm in length.

25. The method of claim 21 wherein said sample area has a centerline that is parallel to and midway between each of said parallel sides, and each of said line lights is at a distance of from about 10 cm to about 25 cm from said sample area centerline.

26. The method of claim 21 wherein each said wedge-shaped light beam intersects said parallel sides to form a wedge angle of from about 15 degrees to about 30 degrees.

27. The method of claim 21 wherein said optical bandpass filter passes light within a wavelength range of about 460 nm to about 480 nm.

28. The method of claim 21 wherein said optical bandpass filter passes light within a wavelength range of about 520 nm to about 540 nm.

29. The method of claim 21 wherein said optical bandpass filter passes light within a wavelength range of about 615 nm to about 635 nm.

30. The method of claim 21 wherein said optical bandpass filter passes light within a wavelength range of about 670 nm to about 690 nm.

31. The method of claim 21 wherein said optical bandpass filter passes light within a wavelength range of about 760 nm to about 780 nm.

\* \* \* \* \*